US011247227B2

(12) United States Patent
Wang et al.

(10) Patent No.: US 11,247,227 B2
(45) Date of Patent: Feb. 15, 2022

(54) APPARATUS, DEVICE AND PROCESS FOR COATING OF ARTICLES

(71) Applicant: Master Dynamic Limited, Shatin (HK)

(72) Inventors: Yingnan Wang, Shatin (HK); Zhuonan Miao, Shatin (HK); Ching Tom Kong, Pat Heung (HK)

(73) Assignee: Master Dynamic Limited, Shatin (HK)

( * ) Notice: Subject to any disclaimer, the term of this patent is extended or adjusted under 35 U.S.C. 154(b) by 465 days.

(21) Appl. No.: 15/185,119

(22) Filed: Jun. 17, 2016

(65) Prior Publication Data

US 2016/0369404 A1 Dec. 22, 2016

(30) Foreign Application Priority Data

Jun. 17, 2015 (HK) .................. 15105780.6

(51) Int. Cl.
*C23C 14/30* (2006.01)
*B05D 1/38* (2006.01)
(Continued)

(52) U.S. Cl.
CPC .............. *B05D 1/38* (2013.01); *A01N 33/12* (2013.01); *A01N 37/02* (2013.01); *A01N 43/16* (2013.01); *B05D 3/107* (2013.01); *C07C 323/52* (2013.01); *C08J 3/24* (2013.01); *C08J 3/28* (2013.01); *C08J 7/18* (2013.01); *C08L 5/08* (2013.01); *C08L 39/00* (2013.01); *C23C 14/024* (2013.01); *C23C 14/14* (2013.01); *C23C 14/225* (2013.01); *C23C 14/30* (2013.01); *C23C 14/34* (2013.01); *C23C 14/505* (2013.01); *C23C 16/4584* (2013.01); *C23C 16/503* (2013.01);
(Continued)

(58) Field of Classification Search
None
See application file for complete search history.

(56) References Cited

U.S. PATENT DOCUMENTS

| 3,859,956 A | 1/1975 | Paola |
| 5,106,346 A | 4/1992 | Locher et al. |

(Continued)

FOREIGN PATENT DOCUMENTS

| CN | 101818326 A | 9/2010 |
| CN | 102057075 A | 5/2011 |

(Continued)

OTHER PUBLICATIONS

English translation for DE19803278.*

(Continued)

*Primary Examiner* — Charles Capozzi
(74) *Attorney, Agent, or Firm* — Kolisch Hartwell, P.C.

(57) ABSTRACT

An apparatus for coating at least a first plurality of articles each article thereof having at least a first surface to be coated is disclosed. The apparatus includes an emission source for directing emission elements towards the first surfaces of the plurality of articles, at least one support member for supporting the first plurality of articles, wherein support member supports the first plurality of articles such that the first surface is exposed to the path of emission from said emission source, and a drive assembly for moving the support member such that the first plurality of articles is moveable with respect to the path of emission from said emission source.

7 Claims, 16 Drawing Sheets

(51) Int. Cl.
*B05D 3/10* (2006.01)
*C23C 14/14* (2006.01)
*C23C 14/22* (2006.01)
*C23C 14/02* (2006.01)
*A01N 37/02* (2006.01)
*A01N 43/16* (2006.01)
*A01N 33/12* (2006.01)
*C23C 14/50* (2006.01)
*C23C 14/34* (2006.01)
*C23C 16/458* (2006.01)
*C23C 16/503* (2006.01)
*C23C 16/505* (2006.01)
*C23C 16/511* (2006.01)
*C07C 323/52* (2006.01)
*C08J 3/24* (2006.01)
*C08J 3/28* (2006.01)
*C08J 7/18* (2006.01)
*C08L 5/08* (2006.01)
*C08L 39/00* (2006.01)
*B05D 1/36* (2006.01)
*B05D 1/18* (2006.01)

(52) U.S. Cl.
CPC .......... *C23C 16/505* (2013.01); *C23C 16/511* (2013.01); *B05D 1/185* (2013.01); *B05D 1/36* (2013.01); *B05D 2201/02* (2013.01); *B05D 2202/40* (2013.01); *B05D 2203/30* (2013.01); *B05D 2350/60* (2013.01); *B05D 2518/00* (2013.01)

(56) References Cited

U.S. PATENT DOCUMENTS

| | | | |
|---|---|---|---|
| 6,509,061 | B1 | 1/2003 | Ida et al. |
| 8,273,180 | B2 | 9/2012 | Wang |
| 8,545,632 | B2 | 10/2013 | Pei |
| 9,113,544 | B2 | 8/2015 | Lau et al. |
| 2002/0062791 | A1 | 5/2002 | Ginovker et al. |
| 2009/0295054 | A1 | 12/2009 | Wu |
| 2010/0314245 | A1 | 12/2010 | Brown et al. |
| 2012/0061558 | A1* | 3/2012 | Lau ........................ B05D 3/007 250/251 |
| 2012/0160162 | A1 | 6/2012 | Wu |

FOREIGN PATENT DOCUMENTS

| | | | |
|---|---|---|---|
| CN | 102414345 A | 4/2012 | |
| CN | 102560381 A | 7/2012 | |
| DE | 19803278 A1 * | 8/1999 | ............... C23C 4/00 |
| EP | 0362418 A1 | 4/1990 | |
| JP | S6328859 | 2/1988 | |
| JP | 2012177191 A | 9/2012 | |
| KR | 20120058843 A | 6/2012 | |
| WO | 2012002473 A1 | 1/2012 | |

OTHER PUBLICATIONS

The Hague, European Patent Office, "Extended European Search Report" in connection with related European Patent Application No. 16001369.4, dated Jan. 19, 2017, 8 pages.

U.K. Intellectual Property Office, "Search Report under Section 72 of the Hong Kong Patents (General) Rules" in connection with related Hong Kong Patent Application No. 15105780.6, dated Nov. 23, 2015, 8 pages.

Wang, Houhua, Authorized Officer, State Intellectual Property Office of the P.R. China, "International Search Report" in connection with related International Application No. PCT/CN2016/086281, dated Sep. 26, 2016, 12 pages.

* cited by examiner

α1+ β1=90 degree; η1+θ1=90 degree.

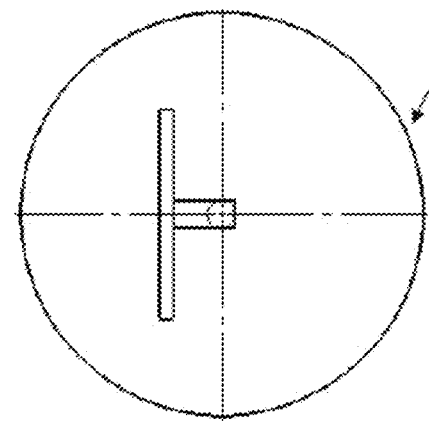 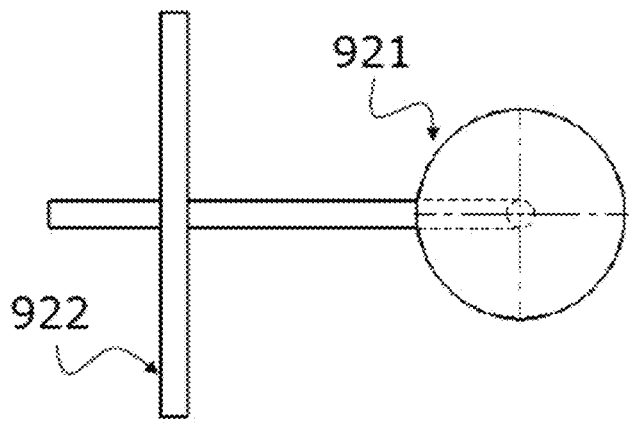
Figure 9a  Figure 9b
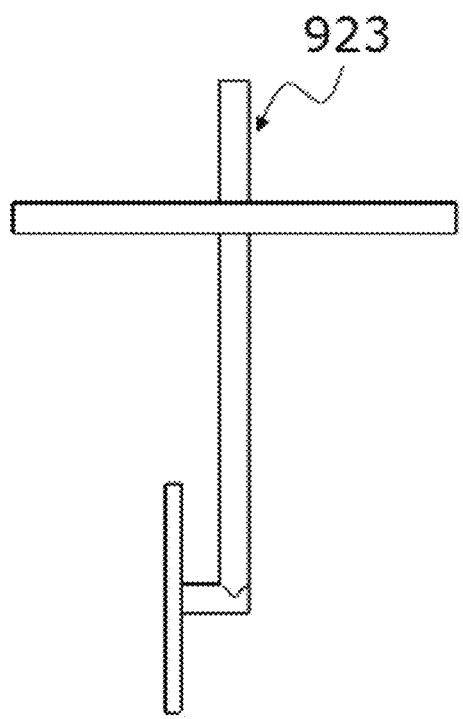
Figure 9c

Figure 12a　　　　Figure 12b

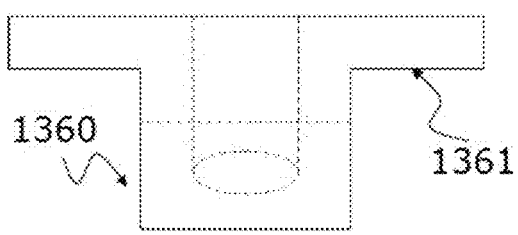
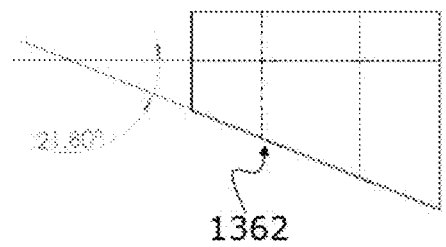
Figure 13a    Figure 13b
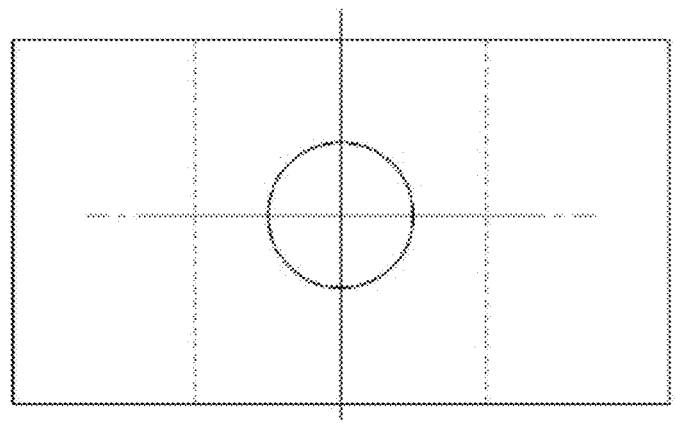
Figure 13c

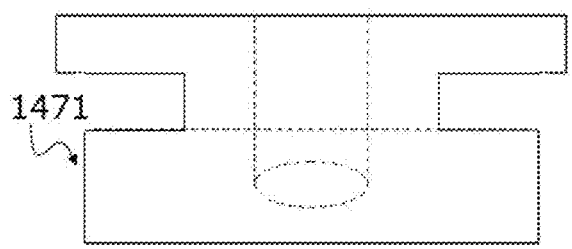
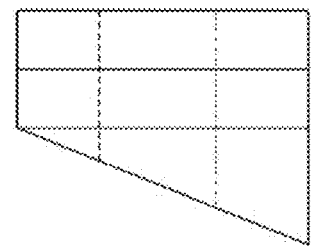
Figure 14a	Figure 14b
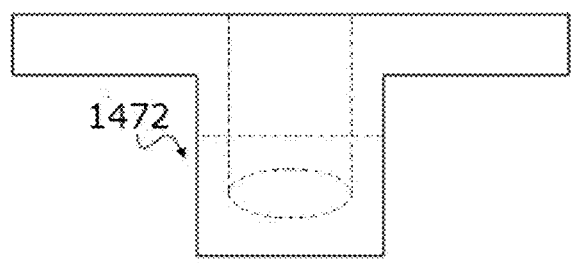
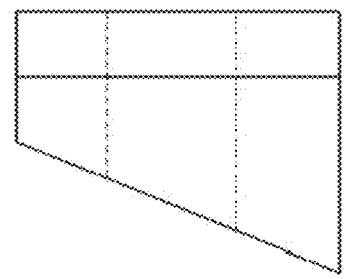
Figure 14c	Figure 14d
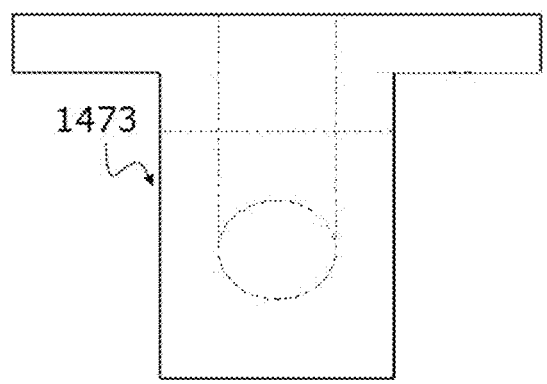
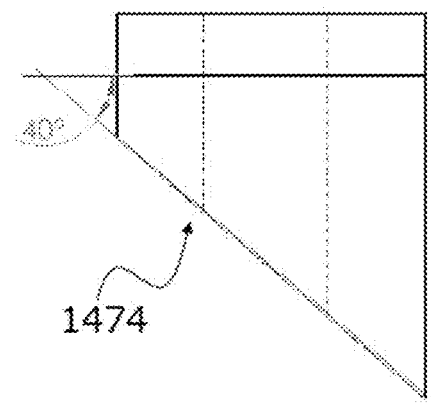
Figure 14e	Figure 14f

APPARATUS, DEVICE AND PROCESS FOR COATING OF ARTICLES

TECHNICAL FIELD

The present invention relates to a process and system for applying a coating to an article and a coated article therefrom. More particularly, the present invention provides a process and a system for applying a coating to an article, such as a decorative or functional coating.

BACKGROUND OF THE INVENTION

In the coating of components or articles which require a coating to be applied to the surface thereof, techniques in the art include discharge and acceleration related techniques which use acceleration of ions or the like.

Within the art, by way of example, mechanical watch components or micro parts typically formed from metal based, silicon based and nickel phosphorous (Ni—P) based materials, may require coating.

Due to high precision and substrate material characteristics, conventional machining and electroplating on metal parts typically cannot meet the critical requirements for high precision and non-conductive based micro parts during fabrication.

Such micro parts can be fabricated by Micro-electromechanical System (MEMS) technology such as Deep Reactive-Ion Etching (DRIE) and Ultraviolet Lithography (Lithography), and Galvanoformung, Abformung (UV-LIGA). Due to the limitation of production capacity and surface finishing requirements for such techniques, methodologies such as sputtering, e-beam or the like may be used in micro part deposition. Within the art, sputtering based deposition techniques are used in MEMS fabrication. These may be controlled through the adjustment of power, DC/RF switch, duration and pressure, for example on film thickness, width, and uniformity control.

For conventional sputtering type deposition, it is typically performed under high value of vacuum, and samples or articles to be coated are fixed to a holder device by way of mechanisms such pressure type fixtures, prior to application of sputtering and introduction to a vacuum chamber or the like.

In such processes of the art, deficiencies exist including the presence of some uncoated blind areas on the samples or articles that pressure fixtures may cover during the sputtering deposition process, and that may cause non-uniformity of coating surface on the back side from the sputtering source. Further, any film or coating may be scratched off relatively easily through hard contact between contact film and pressing fixtures.

For components, samples and articles including those silicon based, difficulty may be experienced using deposition methods of the prior art for the purpose of accurate thickness control, including in nano-scale, as in some application all surfaces of micro parts may be required to be deposited with thin film simultaneously.

In other applications, it is required to apply very thin coatings to articles, such as articles formed from metals or metal alloys, whereby such coatings must withstand at least a nominal amount of abrasive impact without the costings being abraded or worn off the article. Again, in such processes as known in the art, providing such coatings which may be aesthetic or functional and uniformity of thickness, often wear off, debond, or are of a non-uniform thickness

Object of the Invention

It is an object of the present invention to provide an apparatus, device and process for coating of articles, which overcomes or at least partly ameliorates at least some deficiencies as associated with the prior art.

SUMMARY OF THE INVENTION

In a first aspect, the present invention provides an apparatus for coating at least a first plurality of articles each article thereof having at least a first surface to be coated, said apparatus comprising an emission source for directing emission elements towards the first surfaces of the plurality of articles; at least one support member for supporting the first plurality of articles, wherein support member supports the first plurality of articles such that the first surface is exposed to the path of emission from said emission source; and a drive assembly for moving the support member such that the first plurality of articles is moveable with respect to the path of emission from said emission source.

In a first embodiment, the emission source may be a neutral molecular hydrogen flux emission source and the emission elements are neutral molecular hydrogen, whereby the neutral molecular hydrogen flux emission source directs a flux of neutral molecular hydrogen towards the support member, such that upon impact of neutral hydrogen molecules on molecules at or on the surface of an article bonds between elements of the molecules s at or on the surface of an article electively ruptured. Preferably, the neutral molecular hydrogen flux emission source directs a flux of neutral molecular hydrogen having kinetic energies in a range from about 1 eV to about 100 eV towards the support member, such that upon impact of neutral hydrogen molecules on molecules at or on the surface of an article containing any one or combination of C—H bonds and Si—H bonds the C—H bonds and Si—H bonds are selectively ruptured.

The selectively ruptured bonds may cross-link with themselves or with other chemical moieties at said surface resulting in a change in surface properties, or a combination thereof. The selectively ruptured bonds cross-link with themselves or with other chemical moieties at said surface resulting in a change in surface properties, or a combination thereof as to provides a coating on the article.

The apparatus includes a coating chamber in which the articles are coated, and further includes a hydrogen plasma source.

The hydrogen plasma source may be a plasma source selected from the group including a DC plasma, an RF plasma, an ordinary microwave plasma, or an electron cyclotron resonance (ECR) microwave plasma.

In other embodiments, the apparatus may be a sputtering deposition apparatus, or an e-beam evaporation apparatus. The apparatus includes a vacuum chamber, whereby the coating of articles is performed within the vacuum chamber.

In an embodiment of the present invention, the first support member is generally elongate and includes a first plurality of holders for retaining the first plurality of articles along the longitudinal axis of the first support member, wherein the first support member is radially offset from an axis of rotation which is parallel with the longitudinal axis of the first support member and wherein the first plurality of holders extend radially outwardly from the longitudinal axis of the first support member such that the at least first surface of the article inclined at a first inclination to the path of emission from said emission source; and wherein drive assembly rotates the first support about said axis of rotation such that the first plurality of articles is rotated within the path of the emission elements and such that the at least first surface of the articles is exposed to the emission elements from the emission source.

In a further embodiment, the apparatus may include claims, having a first plurality of support members wherein each support member is generally elongate and includes a plurality of holders for retaining the plurality of articles along the longitudinal axis of the first support member, wherein each of the support members is radially offset from an axis of rotation which is parallel with the longitudinal axis of the first support member and wherein the first plurality of holders extend radially outwardly from the longitudinal axis of the first support member; wherein each the axis of rotation of each support member is equally spaced about and radially disposed about first central axis parallel to the longitudinal axes of the generally elongate support members upon a first rotatable platform; and wherein the rotatable platform is rotatable about the first central axis such that each support member is moveable to an exposure position for exposure of the articles to the emission elements.

In yet a further embodiment, the apparatus may include a plurality of rotatable platforms, wherein the rotatable platforms of the plurality of rotatable platforms are equally spaced about a main central axis parallel to the longitudinal axes of the generally elongate support members and the axes of rotation of the rotatable platforms are equally radially offset from the main central axis, and the rotatable platforms are moveable in a circumferential direction about the main central axis so as to be movable into and out of the pathway of the emission elements.

In an alternate embodiment, the support member supports the first plurality of articles extends circumferentially about a central axis of the emission elements and which radial off-set at a first radius and each being equidistant from the central axis said emission source; and wherein the articles are inclined radially inwardly. The first articles are preferably moveably engaged with said support member such that upon rotation of said support member about said central axis the articles at least partly rotate about a second axis of rotation inclined to the first axis of rotation of the support member from gravitational force acting upon the articles, and wherein upon rotation of the support member the articles move from a first position whereby the articles are inclined at the first inclination and on a first inclination surface and inclined to the central axis such that said first surface is exposed to emission from the emission source, to a second inclination and on a second inclination surface and inclined to the central axis such that a second surface of the article opposed to the first surface is exposed to emission from the emission source, and upon further rotation the articles move to the first inclination.

The support member includes an elongate support element extending between the first inclination surface and the second inclination surface, and wherein the support element extends through an aperture or within recess in the article so as to allow the article to slide along the elongate support element from between the support surfaces during rotation about said central axis. The drive assembly for providing said rotational motion about the central axis.

The support member may support a further plurality of articles extends circumferentially about said central axis and are radially off-set at a further radius and each being equidistant from said emission source The emission source may provide a conical shaped emission area having a central axis; and the support member supports the first plurality of articles extends circumferentially about said central axis and a radial off-set at a first radius and each being equidistant from said emission source; and wherein the articles are inclined radially inwardly such that the first surface is inclined at a first inclination substantially normal to the path of emission from said emission source, wherein said first articles are moveably engaged with said support member such that upon rotation of said support member about said central axis the articles at least partly rotate about a second axis of rotation inclined to the first axis of rotation of the support member from gravitational force acting upon the articles, and wherein upon rotation of the support member the articles move from a first position whereby the articles are inclined at the first inclination and on a first inclination surface and inclined to the central axis such that said first surface is exposed to emission from the emission source, to a second inclination and on a second inclination surface and inclined to the central axis such that a second surface of the article opposed to the first surface is exposed to emission from the emission source, and upon further rotation the articles move to the first inclination.

In a second aspect, the present invention provides a process of providing a coating to at least a first plurality of articles, said process including the steps of:
  (i) providing an apparatus according to any one of the preceding claims;
  (ii) providing at least a first plurality of articles to be coated;
  (iii) applying a coating to said at least a plurality of articles.

In a third aspect, the present invention provides a process of providing a coating to at least a first plurality of articles, said process including the steps of:
  (i) applying a surface precursor to the surface of a plurality of articles, wherein said precursor is a precursor from which the coating is to be formed;
  (ii) providing an apparatus according to the first aspect, wherein the emission source is a neutral molecular hydrogen flux emission source; and
  (iii) directing the neutral molecular hydrogen flux from the emission source towards the articles;
wherein upon impact of neutral hydrogen molecules on molecules at or on the surface of an article, the bonds of the precursor are selectively ruptured, and wherein the selectively ruptured bonds cross-link with themselves or with other chemical moieties at said surface resulting in a change in surface properties, or a combination thereof as to provides a coating on the article.

Preferably, the selectively ruptured bonds any one or combination of C—H bonds and Si—H bonds the C—H bonds and Si—H.

In an embodiment of the present aspect, the precursor may be a precursor for forming an antibacterial coating on the article.

In another embodiment, the precursor may be a precursor for forming an anti-wetting coating on the article.

In embodiments of the present aspect, the articles may be an item of jewellery; medical device, medical instrument, implant, hygiene instrument or the like; or a container, vessel, packaging material or the like.

The article may be formed from a metal or metal alloy, such as a precious metal such as from the group including gold, gold based allow, silver, platinum or the like.

Alternatively, the article may be formed from a polymeric material.

The coating applied to the articles may a monolayer of molecules or layer of thickness on the molecular level, such that upon cross linking the coating is optically transparent.

In a fourth aspect, the present invention provides a rotation device for supporting a plurality of articles to be coated from an emission source which emits emission elements; said apparatus comprising:

a first plurality of support members wherein each support member is generally elongate and includes a plurality of holders for retaining the plurality of articles along the longitudinal axis of the first support member, wherein each of the support members is radially offset from an axis of rotation which is parallel with the longitudinal axis of the first support member and wherein the first plurality of holders extend radially outwardly from the longitudinal axis of the first support member and such that the at least first surface of the article inclined at a first inclination to the path of emission from said emission source;

wherein each the axis of rotation of each support member is equally spaced about and radially disposed about first central axis parallel to the longitudinal axes of the generally elongate support members upon a first rotatable platform; and wherein the rotatable platform is rotatable about the first central axis such that each support member is moveable to an exposure position for exposure of the articles to the emission elements.

In an embodiment, the rotation device includes a plurality of rotatable platforms, wherein the rotatable platforms of the plurality of rotatable platforms are equally spaced about a main central axis parallel to the longitudinal axes of the generally elongate support members and the axes of rotation of the rotatable platforms are equally radially offset from the main central axis, and the rotatable platforms are moveable in a circumferential direction about the main central axis so as to be movable into and out of the pathway of the emission elements.

BRIEF DESCRIPTION OF THE DRAWINGS

An example of the invention will now be described with reference to the accompanying drawings, in which:

FIG. 7b depicts the schematic representation of a coating process as shown and as depicted in FIG. 7a;

FIG. 9a shows a bottom view of a schematic representation of a drive assembly according to the present invention for use in the apparatus of FIG. 8a and FIG. 8b;

FIG. 9b shows a side view of the schematic representation of the drive assembly as shown in FIG. 9a;

FIG. 9c shows an end view of the schematic representation of the drive assembly as shown in FIG. 9a and FIG. 9b;

FIG. 10b shows a side view of the schematic representation of the embodiment of the main board holder of FIG. 10a;

FIG. 11b shows a side view of a schematic representation of the embodiment of the main board of FIG. 11a;

FIG. 12a shows a top view of a schematic representation of a further embodiment of a main board according to the present invention;

FIG. 12b shows a side view of a schematic representation of the embodiment of the main board of FIG. 12a;

FIG. 12c shows an end view schematic representation of the embodiment of the inclination element of FIG. 12a;

FIG. 13a shows a top view schematic representation of an embodiment of an inclination element according to the present invention;

FIG. 13b shows a side view schematic representation of the embodiment of the inclination element of FIG. 13a;

FIG. 13c shows an end view schematic representation of the embodiment of the inclination element of FIG. 13a;

FIG. 14a shows a top view schematic representation of a first embodiment of an inclination element according to the present invention;

FIG. 14b shows a side view schematic representation of the embodiment of the inclination element of FIG. 14a;

FIG. 14c shows a top view schematic representation of a second embodiment of an inclination element according to the present invention;

FIG. 14d shows a side view schematic representation of the embodiment of the inclination element of FIG. 14c;

FIG. 14e shows a top view schematic representation of a third embodiment of an inclination element according to the present invention;

FIG. 14f shows a side view schematic representation of the embodiment of the inclination element of FIG. 14e;

FIG. 15a depicts top view a main board of FIG. 12a and FIG. 12b with a plurality inclination elements engaged therewith;

FIG. 15b depicts side view the main board of FIG. 15a;

FIG. 16a shows an end view of a schematic representation of a shutter device according to the present invention for use in the apparatus of FIG. 8a and FIG. 8b;

FIG. 16b shows an end view of a schematic representation of the shutter device as shown in FIG. 16a;

FIG. 17a shows an end view of a schematic representation of an emission source holder according to the present invention for use in the apparatus of FIG. 8a and FIG. 8b; and FIG. 17b shows an end view of a schematic representation of the emission source holder as shown in FIG. 17a.

DETAILED DESCRIPTION OF THE DRAWINGS

Figure 1:
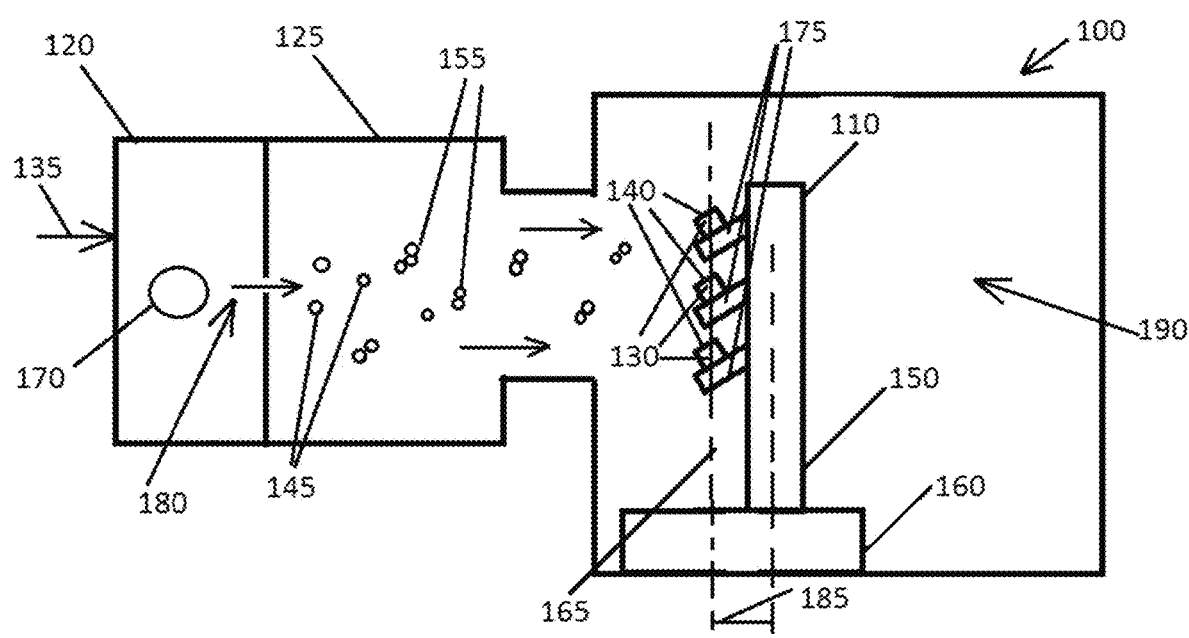
FIG. 1 shows a schematic representation of an embodiment of an apparatus for the coating of articles according to the present invention.

The present invention provides an apparatus, device and process for the application of a coating to the surface of a plurality of articles by way of processes including neutral molecular hydrogen flux emission, sputtering, e-beam evaporation, or other coating techniques which may be utilised for the coating of such articles in accordance with the present invention.

Solutions of the prior art do not provide a uniform coating, in particular for articles which require thin film coating, with deficiencies including variation in optical aspects of the article due to non-uniformity, insufficient "wrap around" whereby the coating does not extend appropriately around an edge of an article giving rise to peeling and debonding of the coating from the article.

Furthermore, solutions of the prior art do not allow for very thin coatings to be readily applied to articles when such a coating is required to be transparent.

The present invention provides solutions to the deficiencies of the prior art by providing an apparatus, system and process which enables a more uniform and well bonded coating to be applied to an article.

The present invention also provides an apparatus, system and process for applying functional coatings to articles, for example antibacterial coatings and anti-wetting coatings, which are sufficiently bonded to an article so as to sufficiently resist abrasion and wear experienced by an article under typical usage, and which in embodiments, is optically transparent.

As such, the present invention provides for coatings which may be functional, decorative, or combinations thereof.

In particular, embodiments of the present invention provides an apparatus, system and process for applying an antibacterial coating which can be applied to an article at a sufficiently low thickness, for example a monolayer or of thickness of the molecular level, such that the coating is optically transparent and does not detract from the optical characteristics. Examples of applicable articles include items of jewellery, time piece components, medical devices, medical instruments, implants, hygiene instruments, containers, vessels, packaging materials or the like.

Such articles may be substantially planar or non-planar, and the present invention provides processes and apparatus for the coating of such articles.

With reference to applications for the coating of watch or timepiece parts or components, such components are often substantially planar with opposed surfaces, whereby one surface or both surfaces may require the application of a coating thereon for particular commercial applications.

For example, in accordance with the present invention, applications include the coating of small scale components for watches or timepieces, metal based, silicon based and nickel phosphorous (Ni—P) materials.

For silicon components, in application of watches and timepieces, a requisite purpose of depositing a layer, is generally for decorative purposes. In particular, a metallic layer may be applied for decorative purposes by way of colour application. Other methods may be utilized so as to achieve different colours on a component formed from silicon, such as depositing silicon nitride with PECVD or LPCVD, or thermal growth of silicon oxide by thermal oxidation. However, such methodologies and processes experience difficulties so as to be impediment for achieving pure colour effects.

By way of example, by depositing silicon nitride on such a component, with the thickness of around 1500 nm, the colour provides a visual appearance of a light gold colour, however the visual appearance is far from providing a visual appearance of a metallic gold surface.

For decoration or decorative purposes in accordance with the present invention for the coating of silicon watch or timepiece components, application of a coating to an article may be by way of sputtering or e-beam evaporation techniques.

As will be understood by those skilled in the art, the present invention is applicable for coatings materials is not limited to metals, but extends to other or alternate materials which may the requirement for application of such coatings, including silicon or silicon based material, for example.

In other aspects of the present invention, the invention may be used for the coating of articles with functional coatings such as anti-bacterial coatings, anti-allergy sensitivity coatings, or non-wetting coatings for example.

In such applications, an article such as an article of jewellery, may have a formulation applied to it initially, which may then be activated or reacted by way of an emission source such as according to the present invention, which causes the coating to activate or set, thus being applied to the surface of the article. Such jewellery articles may be formed from materials such as gold, silver, platinum or the like, without limitation.

Referring to FIG. 1, there is shown a schematic representation of an embodiment of an apparatus 100 for the coating of articles 130 according to the present invention, whereby each article 130 thereof has at least a first surface 140 to be coated.

The apparatus 100 includes an emission source 120 for directing emission elements 155 towards the first surfaces 140 of the of articles 130. At least one support member 110 is provided for supporting the articles 130 such that the support member 110 supports the articles 130 so that the first surface 140 is exposed to the path of emission 155 from the emission source 120.

A drive assembly 160 is provided for moving the support member 110 located in chamber 190 such that the articles 130 are moveable with respect to the path of emission from said emission source 120.

In the present embodiment, the emission source 120 is a neutral molecular hydrogen flux emission source and the emission elements are neutral molecular hydrogen 155. The neutral molecular hydrogen flux emission source 120 directs a flux of neutral molecular hydrogen 155 towards the support member 110, such that upon impact of neutral hydrogen molecules 155 on molecules at or on the surface 140 of the articles 130, bonds between elements of the molecules at or on the surface of an article electively ruptured.

The neutral molecular hydrogen flux emission source 120 includes a hydrogen plasma source 170, with hydrogen gas 130 delivered to the hydrogen flux emission source 120, and hydrogen plasma 145 is accelerated to chamber 125, and neutral molecular hydrogen flux emission is directed towards the articles 130.

The hydrogen plasma source 170 may be a plasma source selected from the group including a DC plasma, an RF plasma, an ordinary microwave plasma, or an electron cyclotron resonance (ECR) microwave plasma.

In an embodiment, the neutral molecular hydrogen flux emission source 120 directs a flux of neutral molecular hydrogen 155 having kinetic energies in a range from about 1 eV to about 100 eV towards the support member 110, such that upon impact of neutral hydrogen molecules on molecules at or on the surface of an article containing any one or combination of C—H bonds and Si—H bonds the C—H bonds and Si—H bonds are selectively ruptured.

The provision of a neutral molecular hydrogen flux emission flux for the breaking of bonds as utilized in the present invention, be provided by the steps as follows for the breaking any one or combination C—H and Si—H molecular bonds in molecules at or on a surface of the article:

(a) forming a plasma and extracting from said plasma a flux of protons having energies in a range from about 50 eV to about 1 keV; thereafter
(b) directing the flux of protons into a chamber and introducing molecules of hydrogen into the chamber;
(c) imparting kinetic energy to said molecules of hydrogen by colliding the protons from said flux of protons with the molecules of hydrogen to produce energetic hydrogen molecules;
(d) producing a flux of neutral molecular hydrogen having kinetic energies in a range from about 1 eV to about 100 eV by cascading collisions between said energetic hydrogen molecules and other hydrogen molecules resulting in all directional scattering of the energetic hydrogen molecules; and
(e) directing the flux of neutral molecular hydrogen to the substrate surface such that upon impact of neutral hydrogen molecules on molecules at or on the surface containing any one or combination of C—H bonds and Si—H bonds the C—H bonds and Si—H bonds are selectively ruptured Upon collision of the neutral molecular hydrogen with the surface 140 of the articles 130, the selectively ruptured bonds cross-link with themselves or with other chemical moieties at the surface 140 resulting in a change in surface properties, or a combination thereof.

There exist different manners in which to perform such a process, and the details of such process including theoretical background, may be referred to in U.S. Pat. No. 9,113,544, from application Ser. No. 13/255,038 to Lau, W. M. Leo et at., and the processes thereof are hereby incorporated by way of cross-reference.

As will be understood by those skilled in the art, other emission sources for various applications may be utilized, without departing from the present invention.

In order to overcome or ameliorate deficiencies of the prior art including those as identified and recited above, in the present embodiment the support member 110 is radially offset 185 from an axis of rotation 165 which is parallel with the longitudinal axis of the support member 110, and a plurality of holders 175 extend radially outwardly from the longitudinal axis of the first support member 110 such that the at the first surface 140 of the article 130 is exposed to the path of emission from said emission source 120.

Upon the drive assembly 160 rotating the support member 110 about the axis of rotation 165, the article 130 are rotated within the path of the emission elements 155 such that the first surface 140 of the articles 130 is exposed to the emission elements 155 from the emission source 120.

As will be understood, in the present embodiment, the axis of rotation 165 extends generally through the centre of the holders 175 such that the holders 175 and articles thereon rotate about the axis of rotation.

Accordingly, the articles are maintained at approximately the same distance from the emission source 120, which results in a more uniform field of emission elements 155 impacting upon the articles 130, resulting in a more even coating on the surface 140 of the articles.

Furthermore, as the articles 130 rotate, more surfaces of the article are exposed to the emission elements, and thus a coating may be applied to substantially the entire outer surface of the articles 130. Furthermore, by inclining the articles to the emission field from the emission source 120 and rotating the articles in the manner as described, increased exposure to aspects of the articles 130 to the emission articles 155 is provides, providing further coverage of a coating to the articles.

The present invention, by providing a more uniform coverage to greater aspects of the articles, results in:
(i) a more uniform colour effect if required,
(ii) a more thickness uniform coating,
(iii) increased "wrap around", which reduces edge peeling and debonding.

Within the present embodiment of the invention with the emission source being a neutral molecular hydrogen flux emission source, it is possible to provide activation of materials on the surface of the articles, whereby bonding between the material and the article is achieved, which provides greater strength and resistance to debonding, wear and dissociation. Such materials applicable include functional materials such as antibacterial coatings and anti-wetting coatings, whereby bonds selectively broken in the antibacterial or anti-wetting material provide for bonding with the article as described above, which a high strength bond and as such, a functional coating may be applied to the articles uniformly and of uniform thickness.

In the present embodiment, deficiencies of the prior art are further address, as when an article has a precursor material applied to its surface prior to exposure to the emission flux whereby the precursor material becomes the coating, a very thin layer of the precursor may be applied of a substantially even thickness. Upon being processed by bond breaking and formation, a coating of a very thin thickness, in the molecular level, results. Such a coating is of a substantial uniform thickness and may be optically transparent, as well as well-bonded.

Figure 2:
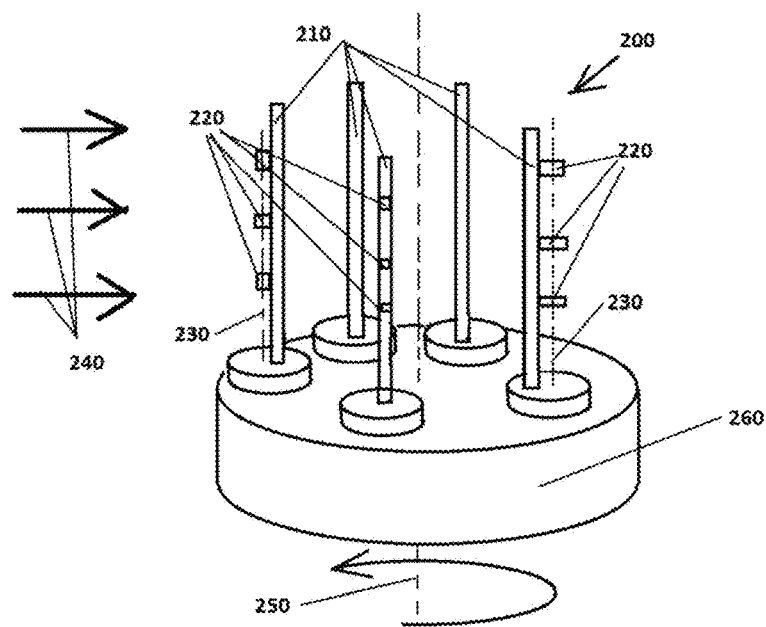
FIG. 2 shows an embodiment of a rotation device according to the present invention.

Referring to FIG. 2, there is shown an embodiment of a rotation device 200 according to the present invention for supporting a plurality of articles to be coated from an emission source. There is provided plurality of support members 210 wherein each support member 210 is generally elongate and includes a plurality of holders 220 for retaining the plurality of articles along the longitudinal axis of the support members 210.

Similarly, as described with reference to FIG. 1, each of the support members 210 is radially offset from an axis of rotation 230 which is parallel with the longitudinal axis of the first support member 210 and wherein the plurality of holders 220 extend radially outwardly from the longitudinal axis of the support members 210 and such that at least a first surface of the articles is exposed to the path of emission 240 from an emission source.

In the present embodiment, each the axis of rotation 230 of each support member 210 is equally spaced about and radially disposed about first central axis 250 which parallel to the longitudinal axes of the support members, and the support members are carried by a first rotatable platform 260.

The rotatable platform 260 is rotatable about the first central axis 250 such that each support member 210 is moveable to an exposure position for exposure of the articles to the emission elements from the emission source.

Figure 3:
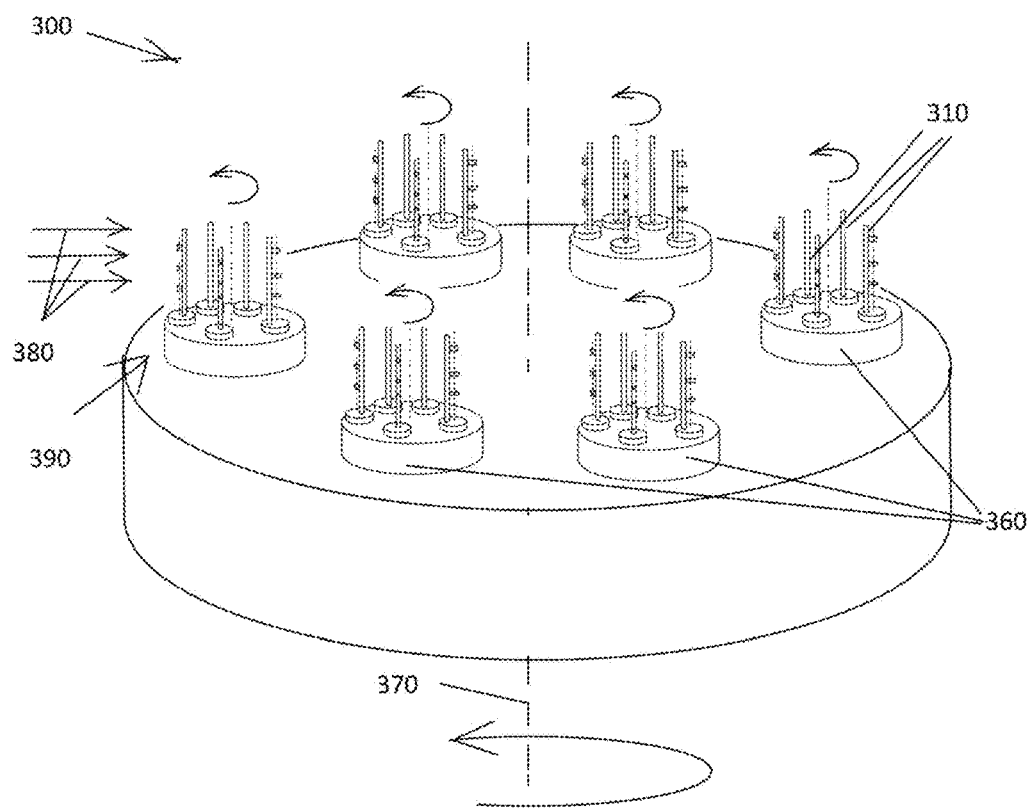
FIG. 3 shows another embodiment of a rotation device according to the present invention for supporting a plurality of articles to be coated from an emission source.

Referring to FIG. 3, there is shown another embodiment of a rotation device 300 according to the present invention for supporting a plurality of articles to be coated from an emission source.

The rotation device 300 includes a plurality of rotatable platforms 360 having a plurality of support members 310, the functionality of which is the same as described with reference to FIG. 2, whereby the support members 310 are radially offset from an axis of rotation and are rotatable thereabout, and the platforms 360 are rotatable about an axis so as to advance the support members 310 to an exposure position 390.

In the present embodiment, rotatable platforms 360 are moveable in a circumferential direction about the main central axis 370 so as to be movable into and out of the pathway of the emission elements 380.

As will be noted, there are three parallel axes of rotation, and the provision of a rotation device of the present embodiment provides for numerous articles to be coated using a coating apparatus such as that of the present invention.

Further, the multi-platform embodiment allows for numerous articles to be placed in a vacuum chamber as is typical for such coating apparatus and such, the set-up time is significantly reduced by not having to reapply an appropriate level of vacuum, as well as not having to re-stabilise the operational temperature and humidity conditions as is required in such coating apparatus. This also contributes to a significant time and cost saving for multiple article coatings, as well as provides the physical advantages over the prior art as discussed above.

Figure 4:
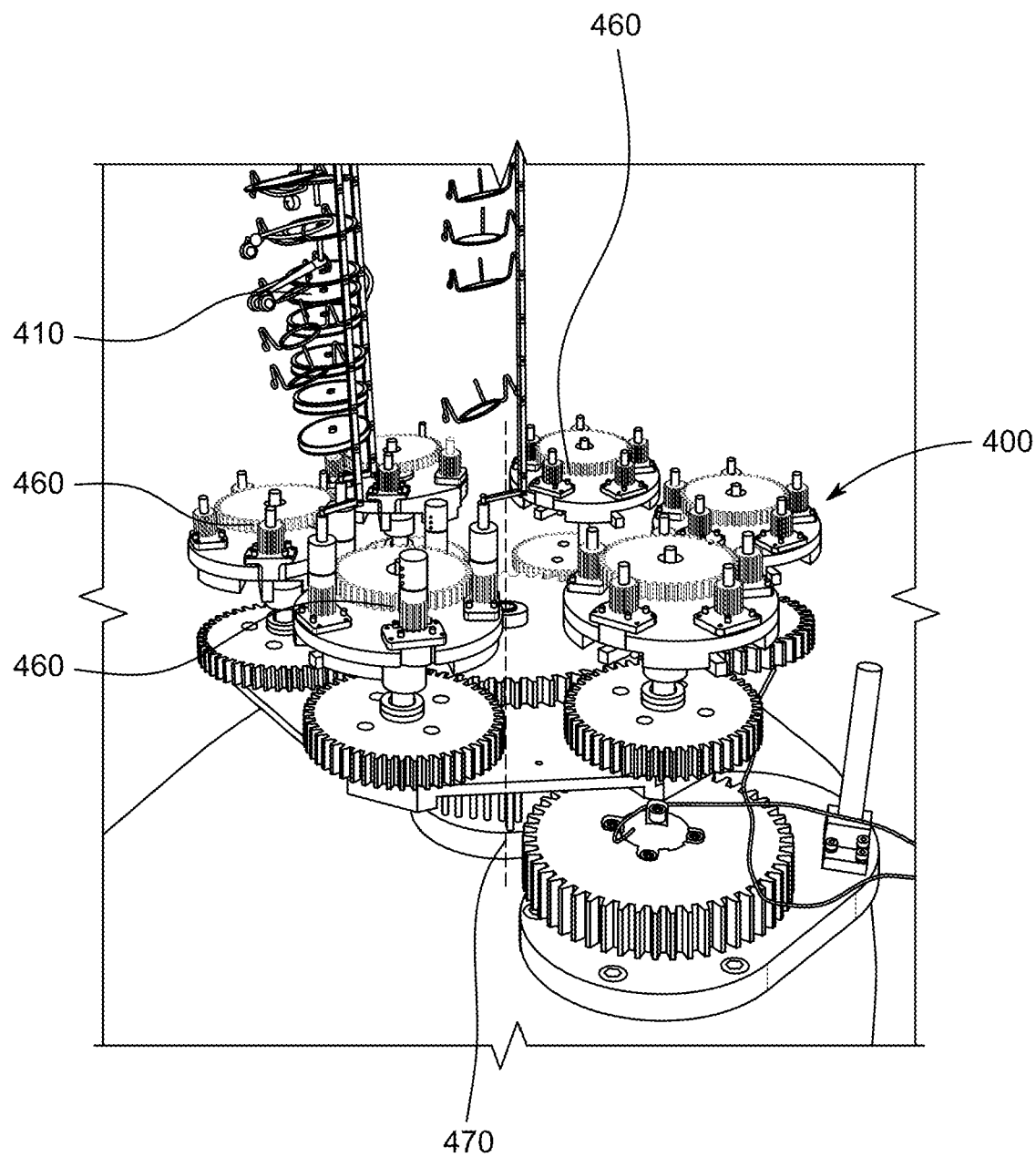
FIG. 4 shows a photographic representation of an embodiment of a rotation device according to the present invention.

Referring to FIG. 4, there is shown a photographic representation of an embodiment of rotation device 400 according to the present invention. The rotation device 400 includes features functionally equivalent to those as shown and described in reference to FIG. 3, whereby the rotation device 400 includes a plurality of rotatable platforms 460 having a plurality of support members 410, whereby the support members 410 are radially offset from an axis of rotation and are rotatable thereabout, and the platforms 460 are rotatable above an axis so as to advance the support members 410 to an exposure position.

The rotational motion as described with reference to FIG. 3 is achieved in the present embodiment by a series of gears, such that all motion is synchronized and centrally controllable external of a vacuum chamber.

Accordingly, the present embodiment allows for the coating of numerous articles, which in addition to the advantages of the coating applied with respect to processes of the prior art, further obviates the necessity for stabilization of vacuum, temperature and humidity, as multiple openings of a vacuum chamber to coat multiple articles of obviated.

Furthermore, as numerous articles may be coated in a single processing stage with a rotation device 400 which provides for accurate and repeatable disposition in the exposure position, resulting in articles with consistent coating quality. A geared mechanism which positions and drives the components of the rotation device provides enhanced control and accuracy of positioning the articles at the exposure position.

Figure 5A:
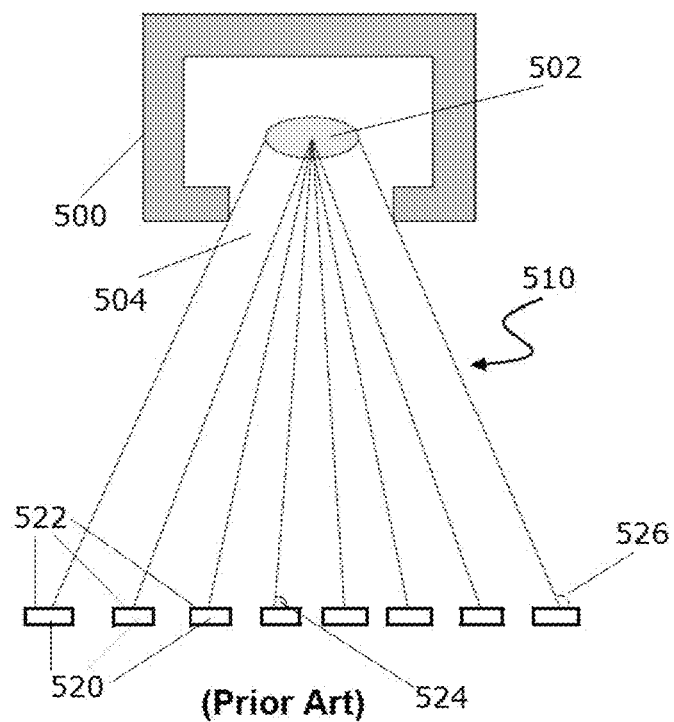
FIG. 5a depicts a schematic representation of a coating process according to the Prior Art.

Referring to FIG. 5a, there is depicted a sputtering process according to the Prior Art. In such a process, there an emission assembly 500 with an emission source 502 and having an aperture 504 through which emission source elements 510, such as ions, are emitted towards articles 520 so as to provide a coating by deposition on a first surface 522 of the articles.

As will be seen, the emission pathways 500 to different articles 520 are different in length, and impact upon different articles 520 at different angles 524 and 526. Such techniques, whilst providing a coating to the first surfaces 522 of the articles 520, provides a non-uniform coating thickness between different articles. Furthermore, a non-uniform coating thickness with a single article 520.

Such non-uniformity results in articles 520 having varying the deficiencies including:

(i) Irregular colour effect between articles in colour type applications. As may be understood, colour effect sensitivity is determined by parameters in particular thickness of coating, and variations in thickness between coatings results in non-uniformity between articles, which results in inconsistently between coloured articles, which results in lack of repeatability and end product items such as timepiece or watch components which may result in variance between end products. This reduces the quality and consistency of end products, and has detrimental market effect.

(ii) Irregular colour effect within a single article has the same effect as between articles as recited at (i), with the additional deficiency that inconsistency may be readily observed without reference to a further article for comparison, again being detrimental to quality.

(iii) Uncoated blind areas on the articles that requisite pressure fixtures may cover an article during the coating process, and that may cause non-uniformity of coating surface on the back side from the sputtering source.

(iv) Film or coating being potentially scratched off relatively easily through hard contact between contact film and pressing fixtures, causing imperfect items and reduction in product yield.

Other deficiencies of the prior art are that there is minimal deposition or coating formation on the edges of the articles, which provides for an aesthetically inferior product, resulting in lower yield and increased inspection time and determination of fulfillment of design requirements.

Furthermore, such techniques of the prior art result in articles with susceptibility for a coating to flake off or debond from the article, due to the thin coating and lack of "wrap-around" to the edges adjacent the surface to which the coating is applied to the articles, resulting in lower yield and increased inspection time and determination of fulfillment of design requirements. This also may result in failure after a period of time, having detrimental commercial effects.

Still further, such prior art techniques require removal of the articles from a substrate to which they are placed, which may compromise the integrity of the coating and create some peeling, again resulting in lower yield and increased inspection time and determination of fulfillment of design requirements.

Yet still further, the prior art does not readily provide for the coating of an opposed surface of an article, which does not allow for "wrap-around" of a coating from the edges, again resulting in potential debonding or delamination between the coating and the article.

Figure 5B:
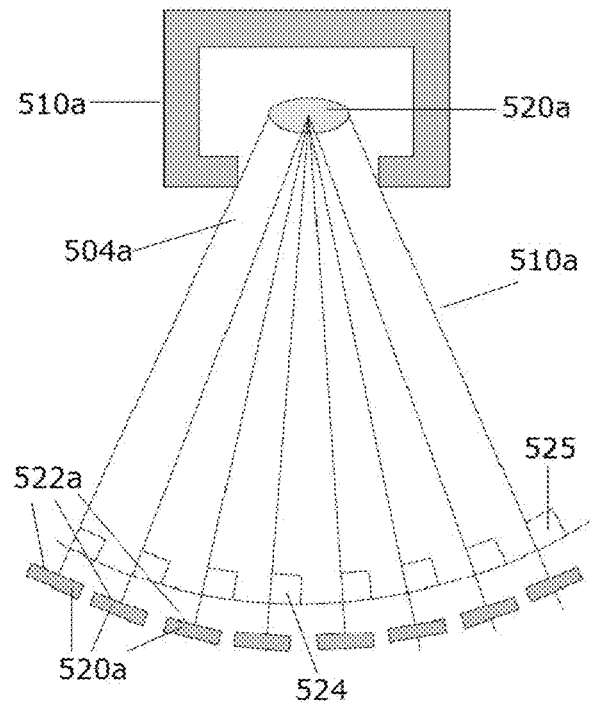
FIG. 5b depicts a schematic representation of a coating process according to the present invention.

Referring now to FIG. 5b, an arrangement of an embodiment of the present invention is shown, for comparative purposes with the Prior Art at FIG. 5a. In such a process, there is an emission assembly 100a with an emission source 502a and having an aperture 504b through which emission source elements 510a, such as ions, are emitted towards articles 520a so as to provide a coating by a process such as a deposition on a first surface 522a of the articles.

As will be seen, the emission pathways 500 to different articles 520 are different in length, and impact upon different articles 520 at different angles 524 and 526. Such techniques, whilst providing a coating to the first surfaces 522 of the articles 520, as provides a non-uniform coating thickness between different articles. Furthermore, a non-uniform coating thickness with a single article 520 results. Such non-uniformity results in articles 520 having varying the deficiencies including those as referred above.

As shown in respect of the present invention, the articles 520a are radially off-set with respect to the emission assembly 500a and the first surfaces 522a of the articles receive exposure to emission source elements 110a more uniformly. In the embodiment as shown, the articles 520a are substantially planar and as such, the angle of incident 525 of the emission source elements 510a with respect to first surfaces 522a is substantially normal, that is perpendicular.

In the present embodiment and as will be readily understood by those skilled in the art, a more even thickness coating may be applied to an article, as well as between articles.

Figure 6:
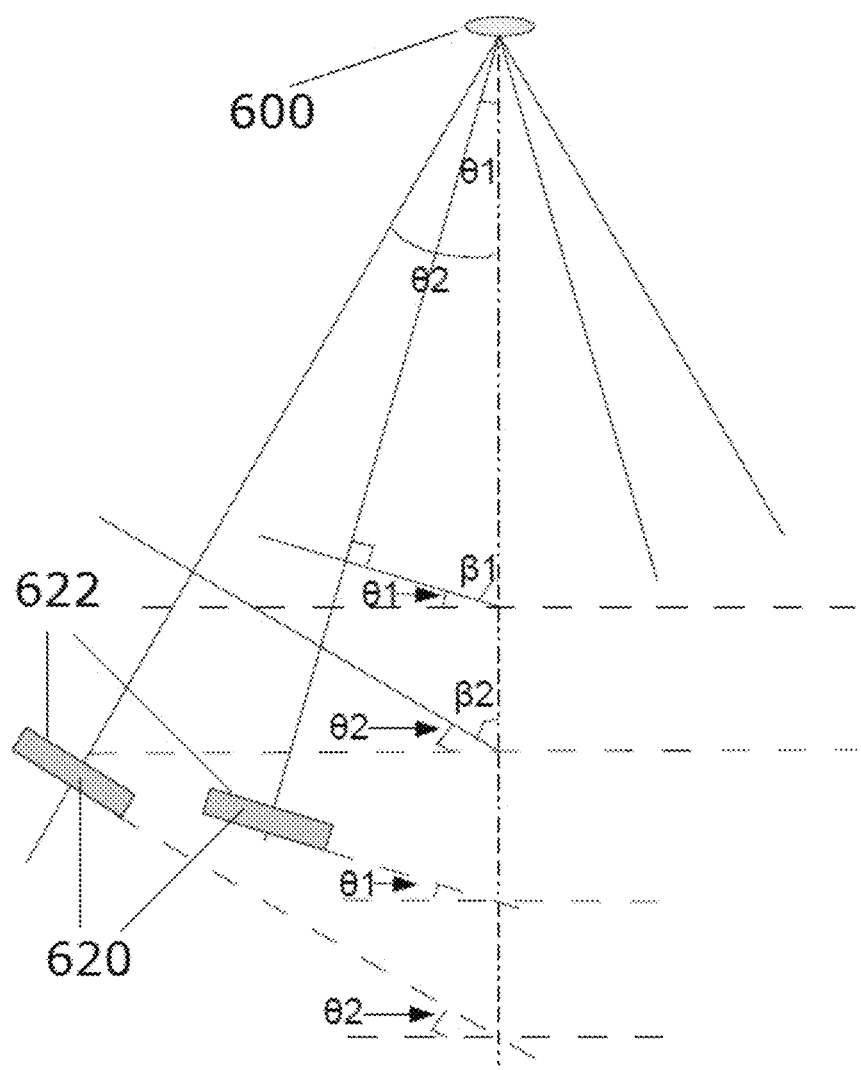
FIG. 6 further depicts a schematic representation of a coating process according to the present invention.

Referring to FIG. 6, based on the location of article 620 from an emission source in accordance with the present invention, the angle of emission path varies. As such, articles 620 are required to be positioned at different angles so as to match or accord with corresponding emission path at a substantially normal angle. In general, the angle between articles 620 and horizontal level should the same as angle between emission path and vertical level.

Figure 7A:
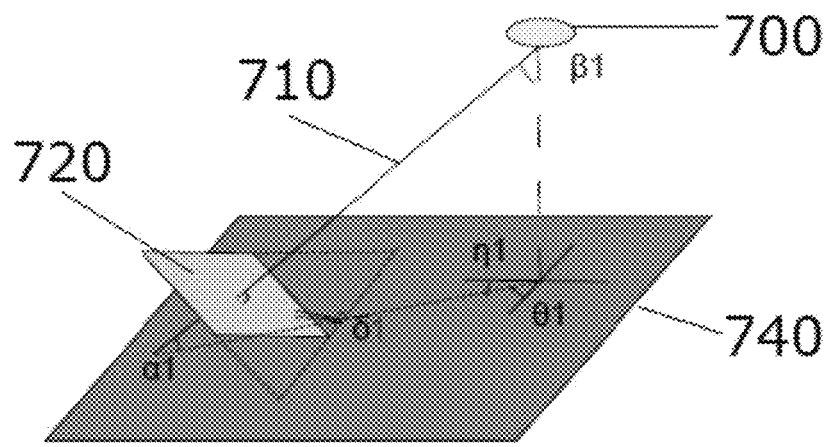
FIG. 7a still further depicts a schematic representation of a coating process according to the present invention.
Figure 7B:
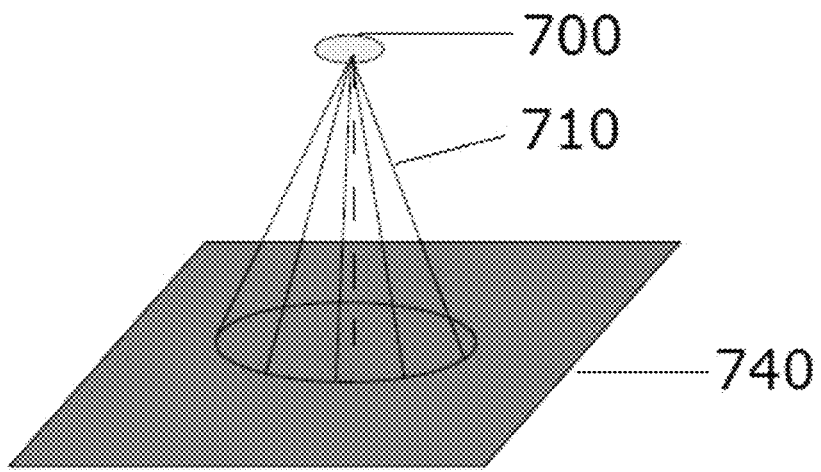

Referring to FIG. 7a and FIG. 7b, in accordance with the present invention, the explosion area of emission is conical shaped, whereby the ions or emission elements with high energy will be emitted from an emission source by a high voltage. Although the emission paths 710 are not uniform, a general mass emission area results within the conical area formed with a substrate 740.

In order to achieve the most uniformity of deposition thickness, the articles 720 are preferably inclined on the arc surface so as to receive emission from a perpendicular emission path as shown in FIG. 6.

Thus, in the present embodiment, the principle of the inclination angle for articles 720 is based on the condition of maintaining emission path perpendicular with the first surface of the articles. As such, when it is required, articles which require the same coating thickness, for example by way of deposition, would be positioned at a same radial distance from the emission source 700 as well as at the same angle of inclination.

Figure 7C:
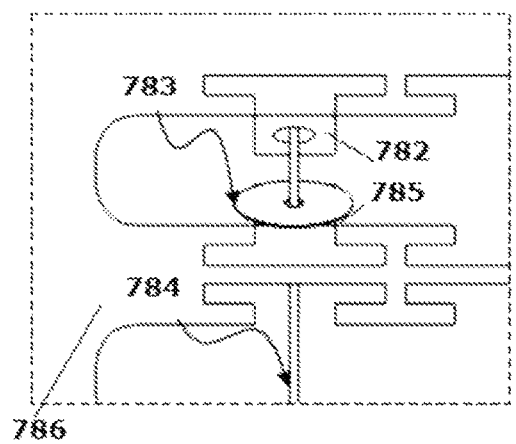
FIG. 7c shows an exemplary embodiment of the manner in which the present invention functions at a first state.
Figure 7D:
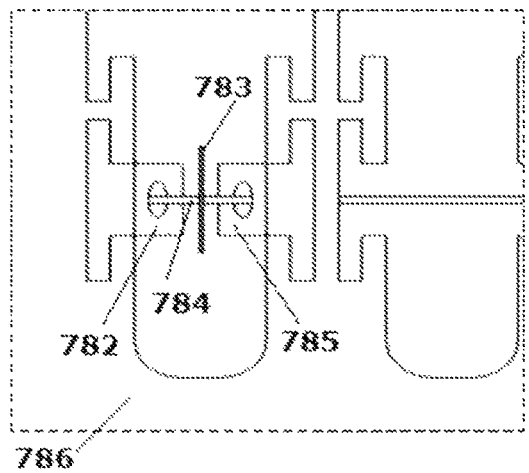
FIG. 7d shows the exemplary embodiment of FIG. 7c at an intermediate state.
Figure 7E:
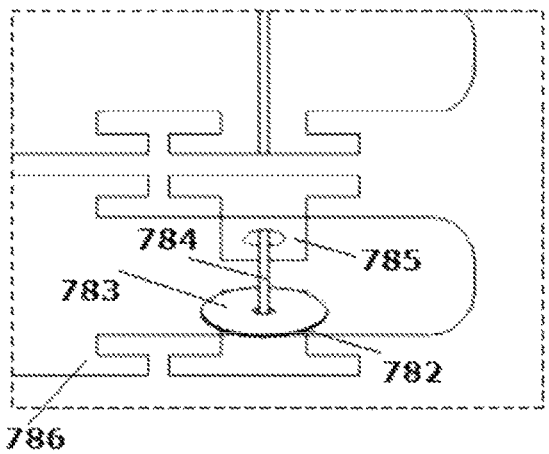
FIG. 7e shows the exemplary embodiment of FIG. 7d and FIG. 7d at a second state.

Referring to FIGS. 7c to 7e, a schematic representation of an embodiment of the present invention is shown, whereby an article 783 to be coated in a matter as described with reference to the inclination angle as described with reference to FIG. 5b to FIG. 5b is depicted, whereby there is shown a portion of a support member 786 with a first inclination element 782, a second inclination element 785, and an article 783 to be coated with a support element 784 providing a first inclination surface extending from the first inclination element 782 to the second inclination element 785 and having a second inclination surface and through an aperture in the article 783. Those skilled in the art will appreciate that the support elements 784, 785 may be integrally formed with the support member 786 and need not be separate elements.

Referring to FIG. 7c, as is shown, the article 783 is generally planar, and is supported by the second inclination element 785 having a first surface of the article 783 engaged with the second inclination element 785.

As is shown in FIG. 7d, when the support member 786 is rotated clockwise or anticlockwise about 90 degrees, within the plane of the page being considered substantially vertical with respect to gravity, the article 783 moves along the support element 784, with which it is slidably engaged therewith, and towards the first inclination element 782.

As is depicted in FIG. 7e, upon further rotation by 90 degrees, the support member 786 has rotated a full 180 degrees, and the article 783 has effectively been flipped over under the effect of gravity such that the second surface of the article 783 is engaged with the first inclination element 782, with the first surface of the article 783 being exposed.

The present embodiment is utilized in conjunction with following embodiments and examples, and allows an article 783 to be:
  (i) Coated on two opposed sides,
  (ii) Coated on its edges,
  (iii) Provide a "wrap-around" of coating from edges to main surfaces,
  (iv) Provides for ease of removal after coating, and minimizing exposure to debonding,
  (v) When used in conjunction with the above embodiment, allows for uniformity of coating thicknesses both between articles and within a single article, and
  (vi) No need for clamping fixtures and thus obviating blind spots effect.

Figure 8A:
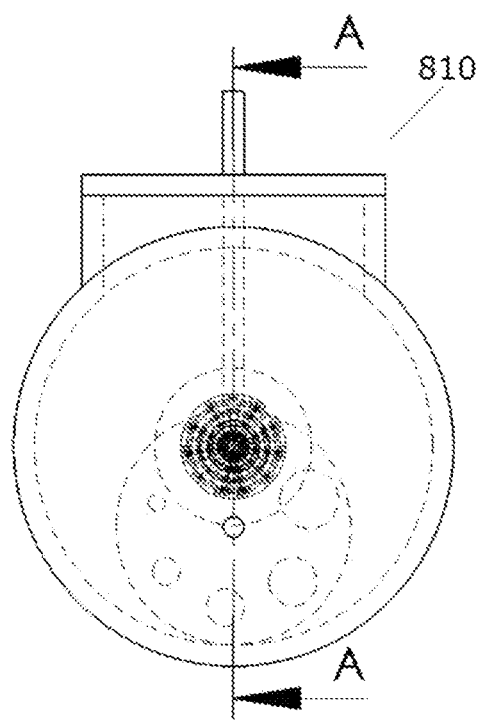
FIG. 8a shows a front view of an embodiment of apparatus according to the present invention.

Referring to FIG. 8a and FIG. 8a, there is shown a schematic representation of an embodiment of an apparatus 810 according to the present invention, for providing a coating to articles, which may be utilized for sputtering based deposition by sputtering for micro parts, for example. Such an apparatus may also be used for coating, as anti-bacterial coatings, anti-allergy sensitivity coatings, or non-wetting coatings, for example.

The apparatus 810 includes a vacuum chamber 811 in which coating such as sputtering based deposition can take place, a base plate 812 that holds the main board holder 816a, a main board 815 which maintains controllable rotation within the vacuum chamber 811, an emission source holder 813 which provides support for target for sputtering deposition, and a rotatable shutter 814 with apertures of different diameters which controls emission area from source holder 813.

Figure 8B:
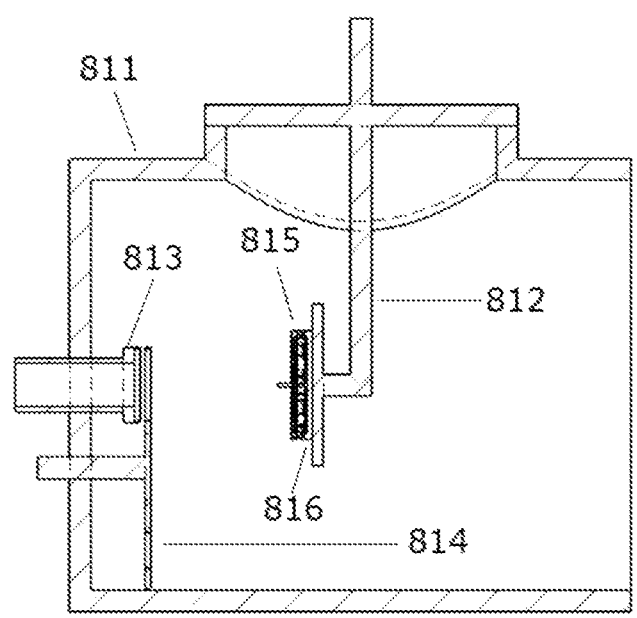
FIG. 8b shows a sectional side view of the apparatus of FIG. 8a along the line A-A.

Referring to FIGS. 9a, 9b and 9c, there is shown a drive assembly 920 suitable for use in conjunction with the apparatus 810 of FIGS. 8a to 8c. The drive assembly includes a lid member 922, which in the present embodiment is provided as being larger than rotation plate 921, and which is used as a seal on the entrance of a vacuum chamber 811 such as that of the apparatus 810 of FIGS. 8a to 8c.

As will be understood by those skilled in the art, wiring and transmission element may be linked with connection rod 923 from ambient environment external to the vacuum chamber 811. The rotation plate 921 is powered so as to be operatively rotatable within the vacuum chamber 811 at variable speeds and intervals, and controlled and programmed external of the apparatus, via an operator for example.

Figure 10A:
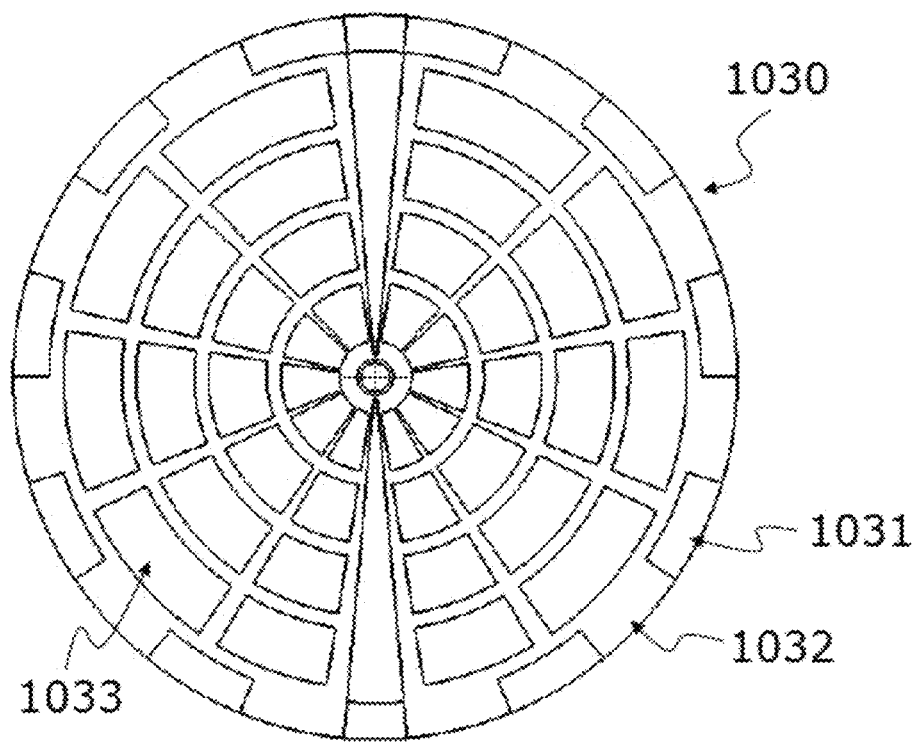
FIG. 10a shows a top view of a schematic representation of an embodiment of a main board holder according to the present invention for use with the drive assembly of FIG. 9a, FIG. 9b and FIG. 9c.
Figure 10B:
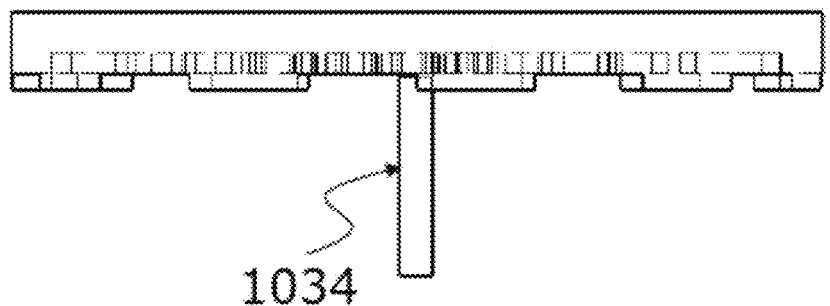

Referring to FIG. 10a and FIG. 10b, there is shown an embodiment of a main board holder 630 according to the present invention, for use with the drive assembly of FIG. 9a, FIG. 9b and FIG. 9c.

As shown, the main board holder 1030 is provided with a circular shape, which allows for use in conjunction with embodiments of the present invention as described with reference to FIG. 5b to FIG. 8 for example. A central rod 1034, step 1031 and slot 1032 are provided for location and fixation of the main board (see FIG. 11a and FIG. 11), a container 1033 is used to store an article and the positioning of each article and for ease of recordation by a marking on the container 633 for article identification. The circular shaped main holder 1030 is designed for use in conjunction with the circular shaped main board 1140 of FIG. 11a and FIG. 11b. The main board holder 1030 is used to retain the main board 1140 and to be installed on the base plate 1012 of FIG. 8 for processing and coating of articles in accordance with the present invention.

Figure 11A:
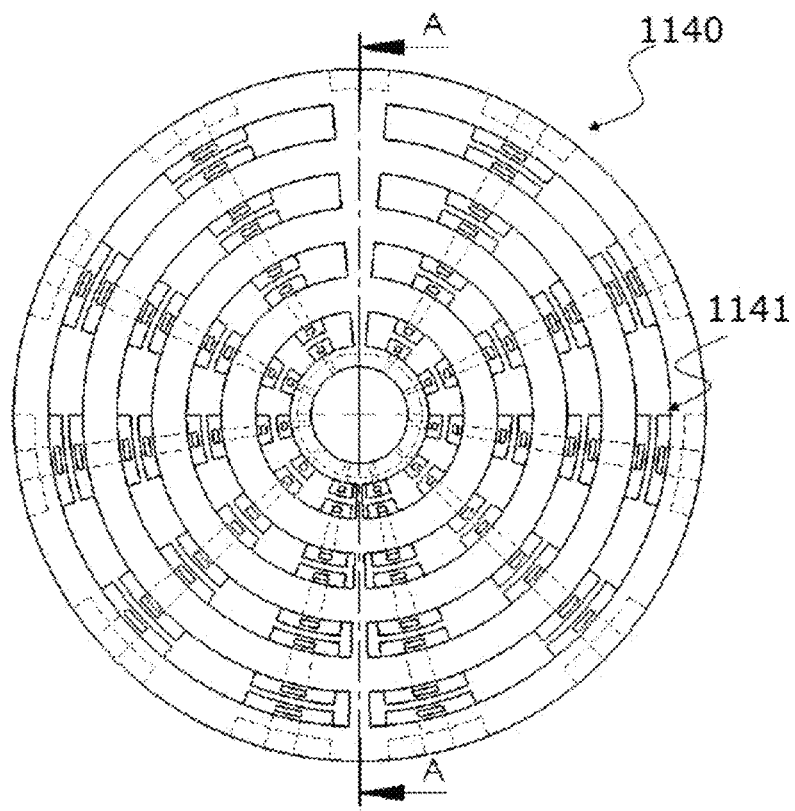
FIG. 11a shows a top view of a schematic representation of an embodiment of a main board according to the present invention for use with the main board holder of FIG. 10a and FIG. 10b.
Figure 11B:
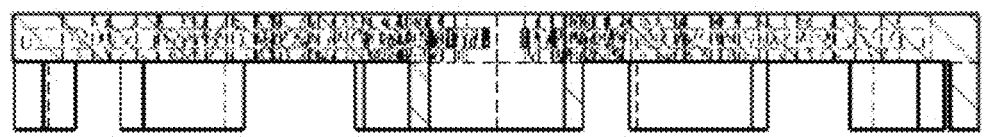

Referring to FIG. 11a and FIG. 11b, a circular shaped main board 1140 is shown, with modules of inclination elements 1141 (see further detail in reference to FIG. 9a to that are assembled such that articles to be coated are to be suspended between the modules of inclination elements 1141, as described above in reference to FIGS. 7c to 7e. For articles for which it is required to have the same coating condition as each other, according to the sizes and deposition thickness requirement of the article, these are to be located on the same circumference at the same radius from the center as each other and inclined in the same manner. In the present embodiment, as shown, there are 4 circles, inner circle, 1st outer circle, 2nd outer circle and the most outer circle, on the main board, 1140 such that articles with different coating requirements may be placed at the appropriate circumference and inclination, so as to provide simultaneous processing.

Figure 12C:
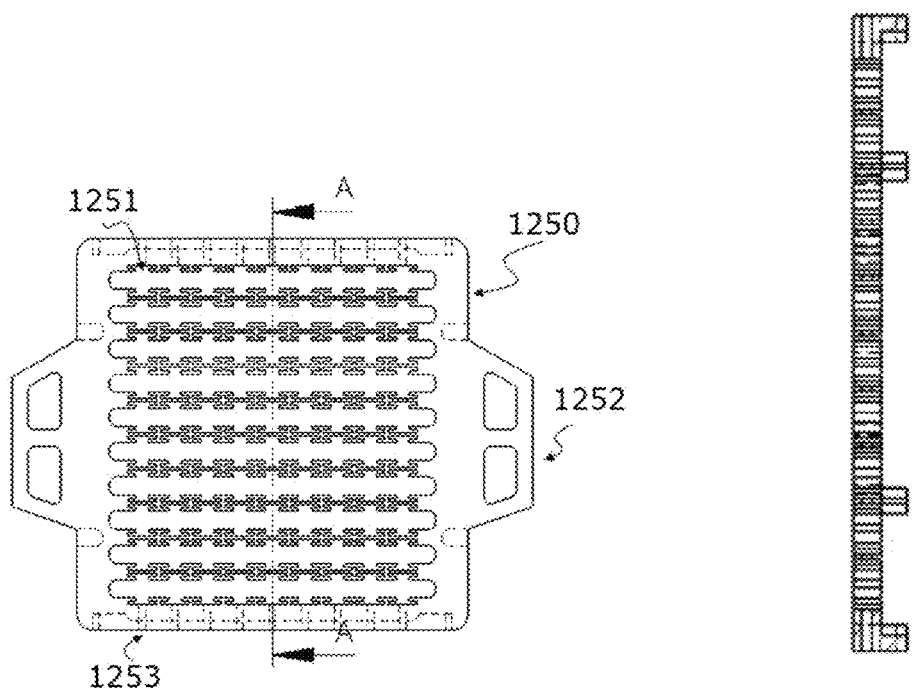
Figure 12C:
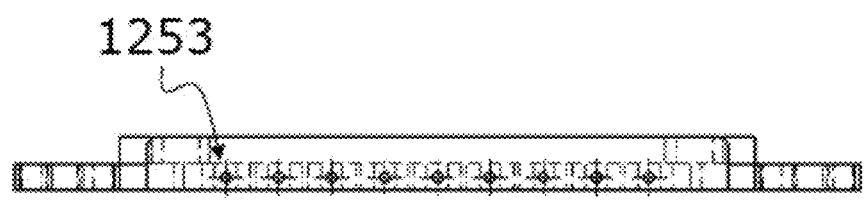

Referring to FIG. 12a, FIG. 12b and FIG. 12c, there is provided a square shaped main board 1250 with empty slots 1251 and handle 1252 as shown. The empty slots 1251 may be used for various inclination element insertion, and the handle 1252 is used for delivery and installation handling. The apertures 1253 are used for support elements which pass through from top to bottom to retain the articles for processing which are engaged between inclination elements. As will be understood, the use of a square shaped main board is applicable for the coating of articles in applications that increased uniformity of coating thickness is not as critical, yet obviating other deficiencies such as masked areas resulting from the processes of the prior art, and as required.

Referring to FIG. 13a, FIG. 13 and FIG. 12c, there is illustrated an embodiment of an inclination element 1360 with a specific width 961 and angle of inclination, are shown. The inclination element 1362 is used to support articles to be coated and for maintaining an inclination orientation during coating, such as by way of sputtering deposition. According to different sizes of articles and location on the main board, various designs may be implemented Referring to FIG. 14a, FIG. 14b, FIG. 14c, FIG. 14d, FIG. 14e and FIG. 14f, three exemplary embodiments of inclination elements with varying inclination angles are shown. As is depicted, the embodiment of FIG. 14a and FIG. 14b 1471 has a larger width than that of FIG. 14c and FIG. 14d 1472 having a smaller width, whereas that of FIG. 10e and FIG. 10f 1073 has a steeper angle of inclination. Those skilled in the art will appreciate that numerous alternate embodiments may be deployed, depending upon the requisite parameters.

Figures 15A, 15B:
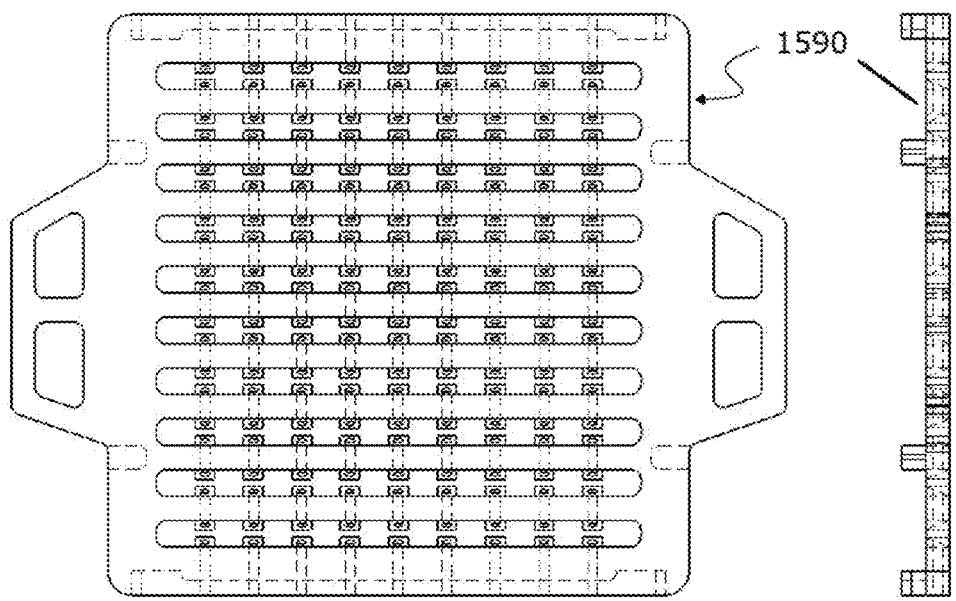
Figure 15C:
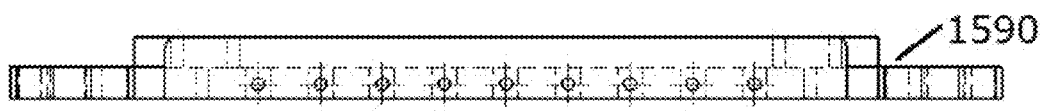
FIG. 15c depicts end view the main board of FIG. 15a and FIG. 15b.

Referring to FIG. 15a, FIG. 15b and FIG. 15c, there is shown a combination of a square main board 1590 similar to that of FIGS. 12a to 12c with inclination elements therein. Such an assembly is operable during a coating process in a manner as described with reference to FIGS. 7c to 7e above, whereby articles are "flipped" during rotation under the effect of gravity.

Figures 16A, 16B:
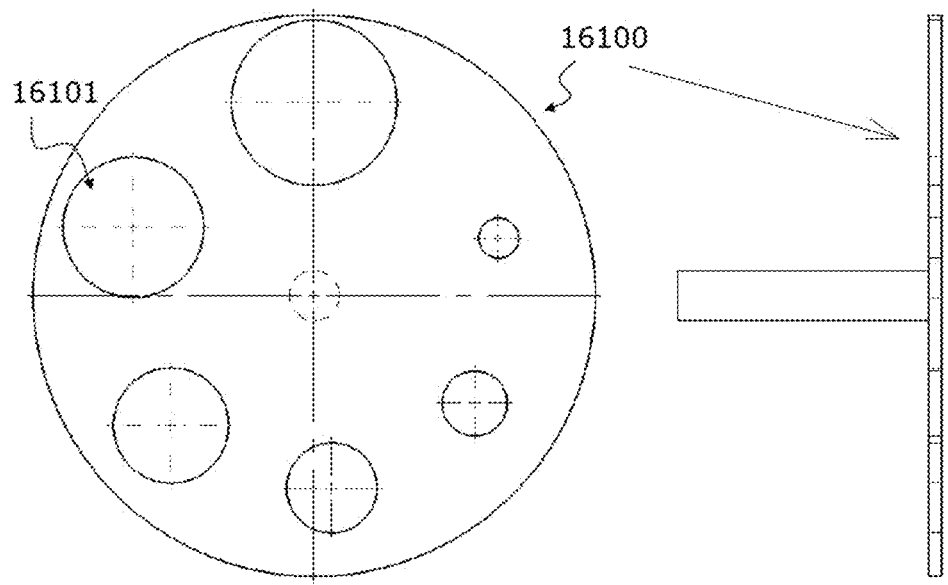

Referring to FIG. 16a and FIG. 16b, there is shown an embodiment of a shutter device 16100 for use in the apparatus of FIGS. 8a and 8b, and having with apertures 16101 of different diameters. The emission elements, such as emission ions from an emission source pass through, or are sputtered in the case of sputter coating, of the apertures 16101 to the surface of a main board in order to effect coating. In order to control the emission area, apertures 16101 are utilised, whereby the shutter device 16100 is rotated so as to align with a requisite aperture 16100 having a requisite different diameter.

Figures 17A, 17B:
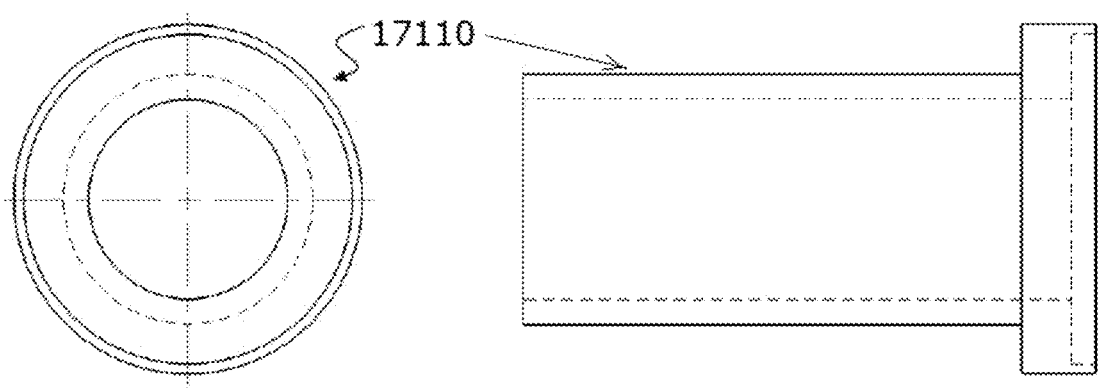

Referring to FIG. 17a and FIG. 16b, an embodiment of an emission source holder 17110 is shown for use for example with the apparatus of FIGS. 8a and 48b, and is used to hold sputtering source such as gold, chrome, and the like.

What is claimed is:

1. An apparatus for forming a coating of a substantially uniform thickness on at least a first plurality of articles, each article thereof having at least a first surface to have said coating formed thereon, wherein the coating of uniform thickness is formed from a precursor material applied to the article of a substantially even thickness prior to the coating of a substantially uniform thickness being formed, said apparatus comprising:

an emission source for directing emission elements towards the first surfaces of the plurality of articles, wherein the emission source is a neutral molecular hydrogen flux emission source and the emission elements are neutral molecular hydrogen;

at least one support member for supporting the first plurality of articles, wherein the at least one support member supports the first plurality of articles such that the first surface is exposed to a path of emission from said emission source; and a drive assembly for moving the at least one support member such that the first plurality of articles are moveable with respect to the path of emission from said emission source;

wherein the at least one support member is elongate and extends normal to the path of emission and includes a first plurality of holders for retaining the first plurality of articles along the longitudinal axis of the at least one first support member, wherein the at least one support member is radially offset from an axis of rotation which is parallel with the longitudinal axis of the at least one support member and that said axis of rotation extends substantially through the center of the holders such that the holders and articles thereon rotate about the axis of rotation, and the articles are maintained at approximately the same distance from the emission source such that a substantially uniform field of emission elements impacting upon the articles is provided, resulting in a substantially even coating on the surface of the articles; and wherein the first plurality of holders extend radially outwardly from the longitudinal axis of the at least one support member such that the at least first surface of the article is inclined at a first inclination to the path of emission from said emission source; and wherein the drive assembly rotates the at least one support member about said axis of rotation such that the first plurality of articles are rotated within the path of the emission elements and such that the at least first surface of the articles is exposed to the emission elements from the emission source; whereby the neutral molecular hydrogen flux emission source directs a flux of neutral molecular hydrogen towards the at least one support member;

wherein such that upon impact of neutral hydrogen molecules on molecules at or on the at least first surface of the article bonds between elements of the molecules at or on the at least first surface of the article are selectively ruptured;

wherein the selectively ruptured bonds cross-link with themselves or with other chemical moieties at said at least first surface resulting in a change in surface properties, or a combination thereof; and wherein the selectively ruptured bonds cross-link with themselves or with other chemical moieties of the precursor material of substantially even thickness at said at least first surface of the articles resulting in a change in surface properties, or a combination thereof so as to provide a coating on the article formed from the precursor material applied to the article of a substantially even thickness prior to exposure to said emission flux, and said coating is of a substantially uniform thickness.

2. An apparatus according to claim 1, wherein the selectively ruptured bonds are any one or combination of C—H bonds and Si—H bonds.

3. An apparatus according to claim 1, wherein the neutral molecular hydrogen flux emission source directs a flux of neutral molecular hydrogen having kinetic energies in a range from about 1 eV to about 100 eV towards the at least one support member.

4. An apparatus according to claim 1, further including a hydrogen plasma source, wherein the hydrogen plasma source is a plasma source selected from the group consisting of a DC plasma, an RF plasma, a microwave plasma, and an electron cyclotron resonance (ECR) microwave plasma.

5. An apparatus according to claim 1, wherein the at least one support member comprises a plurality of support members wherein the support members are elongate and include a plurality of holders for retaining the plurality of articles along the longitudinal axis of the support members, wherein each of the support members is radially offset from the axis of rotation which is parallel with the longitudinal axis of the support member and wherein the plurality of holders extend radially outwardly from the longitudinal axis of the support member;

wherein the axes of rotation of the holders are equally spaced about and radially disposed about a second axis of rotation parallel to the longitudinal axes of the elongate support members of a first rotatable platform; and wherein the rotatable platform is rotatable about the second axis of rotation such that each support member is moveable to an exposure position for exposure of the articles to the emission elements.

6. An apparatus according to claim 5, wherein the apparatus includes a plurality of rotatable platforms, wherein the rotatable platforms are equally spaced about a main central axis parallel to the longitudinal axes of the elongate support members and the axes of rotation of the rotatable platforms are equally radially offset from the main central axis, and the rotatable platforms are moveable in a circumferential direction about the main central axis so as to be movable into and out of the path of the emission elements.

7. An apparatus according to claim 2, wherein the neutral molecular hydrogen flux emission source directs a flux of neutral molecular hydrogen having kinetic energies in a range from about 1 eV to about 100 eV towards the at least one support member.

* * * * *